United States Patent
Mori et al.

(10) Patent No.: US 7,915,431 B2
(45) Date of Patent: Mar. 29, 2011

(54) PROCESS FOR PRODUCTION OF FLAKE-LIKE DRIED 2-(5-ETHYL-5-HYDROXYMETHYL-1,3-DIOXAN-2-YL)-2-METHYLPROPAN-1-OL

(75) Inventors: Naoshi Mori, Okayama (JP); Masafumi Watanabe, Okayama (JP); Junichi Amemiya, Okayama (JP); Ikutaro Kuzuhara, Okayama (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 173 days.

(21) Appl. No.: 12/445,782

(22) PCT Filed: Oct. 10, 2007

(86) PCT No.: PCT/JP2007/069776
§ 371 (c)(1),
(2), (4) Date: Apr. 16, 2009

(87) PCT Pub. No.: WO2008/047651
PCT Pub. Date: Apr. 24, 2008

(65) Prior Publication Data
US 2010/0317878 A1 Dec. 16, 2010

(30) Foreign Application Priority Data
Oct. 17, 2006 (JP) ................................ 2006-282710

(51) Int. Cl.
*C07D 319/06* (2006.01)
(52) U.S. Cl. .......................................................... 549/374
(58) Field of Classification Search ................... 549/374
See application file for complete search history.

(56) References Cited

FOREIGN PATENT DOCUMENTS

| | | |
|---|---|---|
| JP | 54-014365 | 2/1979 |
| JP | 59-134788 | 8/1984 |
| JP | 59-217718 | 12/1984 |
| JP | 62-059104 | 12/1987 |

*Primary Examiner* — Bernard Dentz
(74) *Attorney, Agent, or Firm* — Antonelli, Terry, Stout & Kraus, LLP.

(57) ABSTRACT

A method for producing flake-like dried DOG by making DOG containing from 10 to 50% by mass of a liquid go through a continuous melt-drying step of a specified condition and then making it go through, as a next step, a vacuum-drying step of a specified condition or a ventilation-drying step of a specified condition while holding a molten state thereof, to obtain DOG in which the liquid in DOG is reduced to not more than 0.5% by mass (dried DOG), and flaking the obtained dried DOG in a flake production step.

2 Claims, 1 Drawing Sheet

PROCESS FOR PRODUCTION OF FLAKE-LIKE DRIED 2-(5-ETHYL-5-HYDROXYMETHYL-1,3-DIOXAN-2-YL)-2-METHYLPROPAN-1-OL

TECHNICAL FIELD

The present invention relates to a process for producing flake-like dried 2-(5-ethyl-5-hydroxymethyl-1,3-dioxan-2-yl)-2-methylpropan-1-ol.

BACKGROUND ART 2-(5-Ethyl-5-hydroxymethyl-1,3-dioxan-2-yl)-2-methyl propan-1-ol (hereinafter referred to as "DOG") is represented by the following formula:

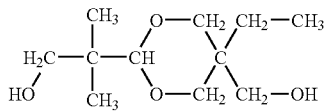

and is a polyhydric alcohol having a special structure having two primary hydroxyl groups, a neo structure and a 1,3-dioxane ring structure. As a method for producing such DOG, for example, a method in which hydroxypivalaldehyde and a trimethylolpropane aqueous solution are subjected to an acetalization reaction in the presence of an acid catalyst such as hydrochloric acid, etc.; after completion of the reaction, the reaction mixture is neutralized with a sodium carbonate aqueous solution or the like; and deposited DOG is obtained by filtration and subsequently dried is disclosed (see Patent Document 1).

Patent Document 1: JP-B-62-059104

DISCLOSURE OF THE INVENTION

Problems to be Solved by the Invention

In subjecting water-containing DOG in a cake form obtained by filtration according to the production method described in Patent Document 1 directly to vacuum-drying as usual drying means, the DOG after drying became a powder having an average particle size of not more than 20 μm [measured by a HELOS KFS type particle size distribution analyzer (manufactured by Sympatec GmbH)] and was difficult in handling as it was. Then, in order to flake such powdered DOG according to a usual flake production method, the present inventors heat-melted the powdered DOG. However, its heat conductivity was poor because of powder, and excessive heating was necessary. In particular, in case of carrying out the production on an industrial scale (for example, 1,000 tons or more per year of dried DOG), deterioration in the purity and quality of DOG due to such excessive heating was noticeable, resulting in a significant problem.

Means for Solving the Problems

In order to solve the foregoing problems, the present inventors made extensive and intensive investigations. As a result, it has been found that in a drying step of DOG containing a liquid such as water, etc., by first going through a continuous melt-drying step which is satisfied with a specified condition and subsequently going through a vacuum-drying step or a ventilation-drying step while holding a molten state, flake-like dried DOG can be produced while keeping the purity and quality of DOG, leading to accomplishment of the present invention.

That is, the present invention provides the following.

(1) A method for producing flake-like dried DOG comprising making DOG containing from 10 to 50% by mass of a liquid (hereinafter sometimes abbreviated as "liquid-containing raw material DOG") go through a continuous melt-drying step as set forth below in (i), to obtain DOG having a liquid content of from 0.8 to 5% by mass (hereinafter abbreviated as "continuously melt-dried DOG"); making the continuously melt-dried DOG go through a vacuum-drying step or a ventilation-drying step while holding a molten state thereof, to obtain DOG whose liquid content is reduced to not more than 0.5% by mass (hereinafter referred to simply as "dried DOG"); and flaking the obtained dried DOG in a flake production step:

(i) Continuous melt-drying step: a continuous melt-drying step of heat melting the liquid-containing raw material DOG in the range of a temperature which is higher of a melting point of the liquid-containing raw material DOG and a boiling point of the liquid, or higher and not higher than 160° C. (hereinafter referred to as "melt temperature range"), to remove the liquid and feeding the residue into a next step and at the same time, continuously or intermittently feeding a non-molten liquid-containing raw material DOG into the molten liquid-containing raw material DOG such that the temperature of the whole liquid-containing raw material DOG does not fall outside the melt temperature range, thereby regulating the liquid content of DOG to be continuously or intermittently fed into a next step to 0.8 to 5% by mass;

(ii) Vacuum-drying step: a vacuum-drying step in which a relation between a temperature X (° C.) and a pressure Y [kPa (abs)] is satisfied with the following expression:

$$10^{(-3708.7/(X+230)+9.11)} \leq Y \leq 0.0025\exp^{(0.0574X)}+10,$$

wherein X is from 125 to 160; and (iii) Ventilation-drying step: a ventilation-drying step of not only ventilating a gas at from 10 to 160° C. for 0.5 hours or more but regulating the total ventilation amount of the gas relative to the continuously melt-dried DOG charged in the ventilation-drying step to 10 times or more (volume ratio) and carrying out the foregoing in the melt temperature range.

(2) The method for producing flake-like dried DOG as set forth above in (1), wherein the liquid is water.

Effect of the Invention

According to the present invention, a flake of DOG whose liquid content is reduced to not more than 0.5% by mass, and if desired, not more than 0.3% by mass can be produced from the liquid-containing raw material DOG without deteriorating the purity and quality. Such flake-like DOG has high quality and is also advantageous in handling.

Figure 1:
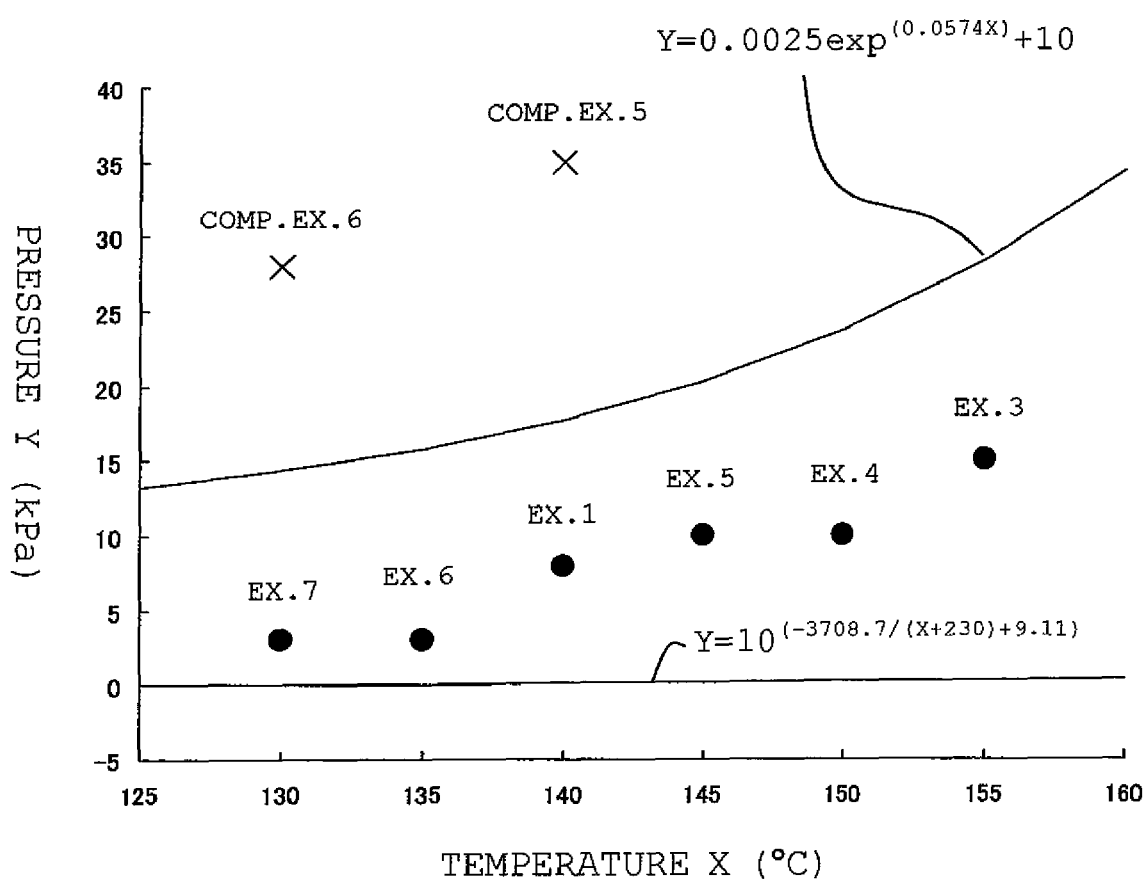
FIG. 1 is a relational graph between a temperature X and a pressure Y of a vacuum-drying step in Examples 1 and 3 to 7 and Comparative Examples 3, 5 and 6.

BEST MODES FOR CARRYING OUT THE INVENTION 2-(5-Ethyl-5-hydroxymethyl-1,3-dioxan-2-yl)-2-methyl propan-1-ol containing from 10 to 50% by mass of a liquid, namely the liquid-containing raw material DOG is not particularly limited regarding a production method thereof and can be produced by a known method such as the method described in Patent Document 1, etc.

For example, a reaction mixture containing hydroxypivalaldehyde (hereinafter referred to as "HPA") obtained by allowing isobutyl aldehyde and a formalin aqueous solution to react with each other in the presence of an alkaline catalyst such as an amine, etc. and if desired, a solvent or HPA obtained through isolation from the reaction mixture is prepared. Such an HPA-containing reaction mixture or HPA after the isolation is allowed to react with trimethylolpropane (hereinafter referred to as "TMP") at from 35 to 60° C. in the presence of an acid catalyst such as hydrochloric acid, etc. and if desired, a solvent. Here, it is preferable from the viewpoint of purity of DOG that a use ratio of HPA and TMP is regulated at HPA/TMP=1.05 to 1.1 (molar ratio). Subsequently, the obtained reaction mixture is neutralized, if desired; and DOG deposited in the reaction mixture is separated by filtration, centrifugation or the like and properly washed with a washing solution, thereby obtaining DOG containing from 10 to 50% by mass of a liquid, and moreover, containing from 18 to 35% by mass of a liquid. For example, the thus obtained DOG contains the solvent used in each reaction or water in the reaction system, and the washing solution used for washing DOG after the separation, etc. These are referred to as "liquid" on the whole in this specification. Specific examples of such a liquid include water; alcohols such as methanol, ethanol, propanol, isopropanol, 1-butanol, 2-butanol, isobutanol, 1-pentanol, 2-pentanol, 3-pentanol, etc.; ethers such as diethyl ether, diisopropyl ether, dibutyl ether, tetrahydrofuran, 1,4-dioxane, etc.; ketones such as acetone, methyl ethyl ketone, 2-pentanone, 3-pentanone, methyl isopropyl ketone, methyl isobutyl ketone, etc.; and the like, and these compounds are compounds having a boiling point of not higher than 160° C. Of these, in case of producing the liquid-containing raw material DOG by the foregoing method, a major component of the liquid is frequently water.

In the present invention, the liquid-containing raw material DOG is first made to go through a continuous melt-drying step as set forth below in (i); by keeping the melt temperature range, the continuously melt-dried DOG is transferred into a next vacuum-drying step or ventilation-drying step while maintaining a molten state thereof; the transferred DOG is made to go through either one of these steps, thereby obtaining dried DOG having a liquid content of not more than 0.5% by mass; and the obtained dried DOG is flaked in a flake production step, thereby producing flake-like dried DOG.

(i) The continuous melt-drying step as referred to herein is a continuous melt-drying step of <A> heat-melting the liquid-containing raw material DOG in the foregoing melt temperature range, to remove the liquid and feeding the residue into a next step and <B> at the same time, continuously or intermittently feeding a non-molten liquid-containing raw material DOG into the molten liquid-containing raw material DOG such that the temperature of the whole liquid-containing raw material DOG does not fall outside the foregoing melt temperature range, thereby <C> regulating the liquid content of DOG to be continuously or intermittently fed into a next step to 0.8 to 5% by mass.

First of all, the continuous melt-drying step as set forth above in (i) is described.

Re <A>: The liquid-containing raw material DOG is heat-melted in the range of a temperature which is higher of a melting point of the liquid-containing raw material DOG and a boiling point of the liquid, or higher and not higher than 160° C. (melt temperature range), thereby reducing the liquid content of DOG to 0.8 to 5% by mass, and the resulting DOG is fed into a next step. Though the melting point of the liquid-containing raw material DOG varies depending upon the kind of the liquid or the liquid content, and even when such is taken into consideration, it is in the range of from 100 to 125° C. In order to always keep DOG in a molten state in this drying step, it is necessary to regulate the temperature at lowest at the melting point of the liquid-containing raw material DOG or higher. Also, the liquid contained in the liquid-containing raw material DOG cannot be efficiently removed unless the temperature is the melting point of the liquid or higher. On the other hand, when the temperature exceeds 160° C., decomposition of DOG or the like occurs, whereby the yield or purity is liable to be deteriorated. When the temperature is not higher than 160° C., it is possible to attain a purity of dried DOG finally obtained in the present invention of 95% by mass or more, and the quality of dried DOG can be kept high.

A rate of feeding into the next step is the same as a rate of feeding a non-molten liquid-containing raw material DOG into the molten liquid-containing raw material DOG as set forth below in <B>.

Re <B>: A non-molten liquid-containing raw material DOG is continuously or intermittently fed into the molten liquid-containing raw material DOG such that the temperature of the whole liquid-containing raw material DOG does not fall outside the foregoing melt temperature range. So far as the starting time of melt-drying is concerned, the liquid-containing raw material DOG melted within an apparatus is first produced according to the foregoing <A>, and a non-molten liquid-containing raw material DOG which is the raw material is continuously or intermittently fed into the apparatus. So far as the melt-drying is continued, since the molten liquid-containing raw material DOG is already present in the apparatus, the non-molten liquid-containing raw material DOG may be merely continuously or intermittently fed into the apparatus.

In this way, since heat efficiently conducts into the liquid-containing raw material DOG, excessive heating is not necessary; it is possible to attain a purity of dried DOG finally obtained in the present invention of 95% by mass or more; and the quality of dried DOG can be kept high.

As a method for make the temperature of the whole liquid-containing raw material DOG not fall outside the foregoing melt temperature range, it is preferable that a rate of feeding the non-molten liquid-containing raw material DOG and a rate of feeding the molten liquid-containing raw material DOG into a next step are regulated, thereby controlling a retention time of the molten liquid-containing raw material DOG within the apparatus at from 0.5 to 6 hours; and from the viewpoint of efficiently and stably carrying out the continuous melt-drying, the retention time is more preferably from 1 to 4 hours.

The continuously molten DOG in the apparatus is taken out depending upon the feed rate of the liquid-containing raw material DOG and transferred into a next step, thereby continuously carrying out the melt-drying step.

Re <C>: By carrying out the foregoing <A> and <B>, the liquid content of DOG to be continuously or intermittently fed into a next step (hereinafter referred to as "continuously melt-dried DOG") is regulated at from 0.8 to 5% by mass. DOG is used as a raw material or intermediate of various chemicals, such as a raw material of acrylate compounds, etc.; and it is known that in such an application, when the liquid content is from 0.8 to 5% by mass, a side-reaction or decomposition of DOG occurs, and it is the actual situation that DOG is usually an off-spec as a product. However, since the foregoing <B> is carried out, in order to feed DOG in which the liquid is reduced to less than 0.8% by mass into a next step, the retention time must be prolonged. Thus, the drying efficiency becomes worse so that it is not practical to carry out the production on an industrial scale. Then, in this step, the liquid content of DOG is held within the range of from 0.8 to 5% by mass.

The apparatus which is used in the continuous melt-drying step is not particularly limited, and examples thereof include a stirring tank having a heating function, a heat exchanger and an extruder. The continuous melt-drying step is carried out under atmospheric pressure. In case of a stirring tank having a heating function, stirring means of a DOG melt may be a stirring blade rotating around an axis, an apparatus which rotates itself or an apparatus a main body of which vibrates. Examples of the stirring blade include a semicircular blade, a paddle blade, a turbine blade, an anchor blade and a ribbon blade. The heating function is imparted by steam, electric power, a heating medium, etc.

After the foregoing continuous melt-drying step, by subjecting the obtained continuously melt-dried DOG to, as a next step, the vacuum-drying step as set forth above in (ii) or the ventilation-drying step as set forth above in (iii), DOG in which the liquid content is reduced to not more than 0.5% by mass, and if desired, not more than 0.3% by mass can be obtained. In transferring from the continuous melt-drying step to the next step, it is important to maintain the continuously melt-dried DOG in a molten state while keeping it within the melt temperature range.

In order to control the liquid content of the liquid-containing raw material DOG at not more than 0.5% by mass only by the vacuum-drying step without going through the continuous melt-drying step, a large-sized vacuum-drying apparatus is necessary in carrying out the step on an industrial scale (for example, 1,000 tons or more per year of dried DOG), and furthermore, the drying efficiency is poor. Therefore, such is not a suitable method in view of cost and is not practical. Also, in order to remove a large amount of the liquid to a degree of not more than 0.5% by mass only by the ventilation-drying step, a massive amount of a gas is necessary, and such is not practical, too. However, according to the present invention, in producing flake-like DOG which is required to have high quality, it has been successful to stably produce thoroughly dried DOG at low costs without dropping the quality over a long period of time by utilizing a combination of the continuous melt-drying step with the vacuum-drying step or ventilation-drying step.

In the vacuum-drying step, from the viewpoint of driving drying of the continuously melt-dried DOG, it is necessary that the vacuum-drying temperature X (° C.) and the pressure Y [kPa (abs)] are satisfied with the following expression:

$$10^{(-3708.7/(X+230)+9.11)} \leq Y \leq 0.0025\exp^{(0.0574X)}+10,$$

wherein X is from 125 to 160. So far as such a vacuum-drying condition can be maintained, the vacuum-drying step may be carried out in any of a batchwise manner or a continuous manner. Also, a method for reducing the pressure is not particularly limited, but the pressure reduction may be achieved by a vacuum pump or an executor.

The apparatus which is used in the vacuum-drying step is not particularly limited, and examples thereof include a stirring tank having a vacuum function and a heating function, a distillation apparatus, a heat exchanger and a drying machine.

In the ventilation-drying step, from the viewpoint of driving drying of the continuously melt-dried DOG, it is necessary that a gas at from 10 to 160° C. is ventilated for 0.5 hours or more while keeping the continuously melt-dried DOG at from 125 to 160° C., and it is more preferred to perform the ventilation for one hour or more. Though the ventilation time is not limited as to its upper limit, a time within 12 hours is in general sufficient. As the gas to be ventilated, a gas which is inert against the liquid and DOG is preferable, and examples thereof include air, nitrogen, helium, argon and carbon dioxide. Of these, it is preferred to use nitrogen. The total ventilation amount of the gas relative to the continuously melt-dried DOG as fed is 10 times or more, preferably from 50 to 500 times, and more preferably from 100 to 300 times in terms of a volume ratio. The volume of the continuously melt-dried DOG which is fed into the ventilation-drying step can be calculated by diving a mass by a specific gravity. Also, so far as such a ventilation-drying condition can be maintained, the ventilation-drying step may be carried out in either of a batchwise manner or a continuous manner. So far as the liquid is thoroughly removed by regulating the temperature of the gas after the ventilation at not higher than its dew point, the thus obtained gas may be circulated and used. The apparatus which is used in the ventilation-drying step is not particularly limited and may be an apparatus equipped with a heating function and a ventilation apparatus.

The thus obtained dried DOG is molded in a flake form by a flaker chiefly for the purpose of convenience in handling. Here, in feeding into a flaker, it is important to hold the dried DOG in a molten state. The flaker is not particularly limited but may be, for example, any of a drum flaker, a belt flaker, a table flaker, etc. From the viewpoints of installation area, production capability and operability, it is preferred to use a drum flaker.

Though a feed mode of the dried DOG into the flaker is not particularly limited, a top feed mode or a dip feed mode, each of which does not require special equipment, is preferable. From the viewpoint of production capability of the flake, in general, the temperature of a cooling medium of the flaker is preferably from 5 to 60° C., and more preferably from 10 to 50° C. Though the cooling medium to be used is not particularly limited, water is general. Also, the flaking may be properly hastened using cool air. In forming a flake, a rotation rate of the drum or belt or the like is not particularly limited, but a rate at which the flake can be produced may be properly chosen. For example, it is preferably from 0.5 to 20 m/min, and more preferably from 1 to 10 m/min. Though the size of the flake-like dried DOG is not strictly limited, an area of the surface portion is preferably from 0.05 to 10 $cm^2$, and more preferably from 0.1 to 4 $cm^2$. Also, its thickness is preferably from 0.2 to 5 mm, and more preferably from 0.3 to 3 mm. The size of the flake-like dried DOG falling within the foregoing range is preferable because the flake is hardly pulverized so that the generation of a fine powder is scarce, and furthermore, its solubility is satisfactory, whereby the dried DOG which is easily usable is available.

EXAMPLES

The present invention is hereunder described in more detail with reference to the Examples and the like, but it should not be construed that the present invention is limited thereto. The purity of DOG was calculated as follows.

[Purity of DOG]

The purity (% by mass) of DOG in the dried DOG was calculated according to a calculation expression: "[100−{water content (% by mass) of dried DOG}]×{DOG concentration (% by mass) in residual components from which water in the dried DOG has been eliminated}/100".

The measurement of the water content in the dried DOG was carried out using a Karl Fischer's moisture titrator (MKA-610 Model, manufactured by Kyoto Electronics Manufacturing Co., Ltd.). Also, the DOG concentration (% by mass) in the residual components from which water in the product had been eliminated was determined by dissolving the dried DOG in acetone in a concentration of 45 mg/1.5 mL and analyzing the solution under the following gas chromatographic analysis condition.
[Gas Chromatographic Analysis Condition]
Apparatus: GC-1700 (manufactured by Shimadzu Corporation)
Used column: DB-1 (manufactured by Agilent Technologies)
Analysis condition: Injection temperature: 220° C.
  Detection temperature: 270° C.
Column temperature: Temperature rise from 140° C. to 180° C. at a rate of 1° C./min→Keeping at 180° C. for 10 minutes→Temperature rise to 270° C. at a rate of 20° C./min→Continuation at 270° C. for 5 minutes
Detector: Hydrogen flame ionization detector (FID)

Referential Example 1

Isobutyl aldehyde and formaldehyde were allowed to react with each other in the presence of triethylamine, thereby obtaining a mixture consisting of 64.32% by mass (corresponding to 0.5896 moles) of HPA, 1.10% by mass of isobutyl aldehyde, 4.08% by mass of methanol, 2.57% by mass of triethylamine, 26.53% by mass of water and 1.40% by mass of an unknown material (hereinafter referred to as "HPA mixture").

182.5 parts by mass of a TMP aqueous solution [72.5 parts by mass (corresponding to 0.540 moles) of TMP and 110 parts by mass of water] and 5.0 parts by mass of 35% by mass hydrochloric acid were mixed, to which was then added 93.5 parts by mass of the HPA mixture at 55° C. under a normal pressure over 4 hours, and after the addition, stirring of the mixture was continued for an additional 3 hours. After elapsing about 0.5 hours after the start of the reaction, a part of the formed DOG was crystallized, and the reaction mixture became a cloudy slurry state. As the reaction proceeded, this state became remarkable, and after 7 hours, the mixture became a slurry state to an extent that the stirring efficiency was lowered. After completion of the reaction, a 10% by mass sodium carbonate aqueous solution was added, thereby performing neutralization until the pH of the reaction mixture reached 7.2. After the neutralization, the mixture was filtered, thereby separating DOG as a cake. There was thus obtained 113.1 parts by mass of liquid (water)-containing raw material DOG (water content: 23% by mass).

Example 1

Continuous Melt-Drying Step

In a stirring tank having an internal volume of 1 L, 600 g of the liquid-containing raw material DOG (water content: 23% by mass) as obtained in Referential Example 1 was charged and heated under a normal pressure until it was melted. On that occasion, a temperature at the point of time when the liquid-containing raw material DOG was completely melted (melting point of the liquid-containing raw material DOG) was 105° C. Furthermore, the temperature of the stirring tank was heated to 140° C. and kept at that temperature. The liquid-containing raw material DOG was fed and continuously melt-dried under the following condition.
[Melt-Drying Condition]
Feeding and discharging conditions of liquid-containing raw material DOG: To feed every 50 g at intervals of 10 minutes 36 times and to discharge every 50 g at intervals of 10 minutes 36 times
Stirring rotation number: 200 rpm
Fluidization means: Semicircular blade rotating around an axis
Temperature: 140° C.
Pressure: Normal pressure
Time: 6 hours As a result of continuously melt-drying the liquid-containing raw material DOG under the foregoing condition, 1,800 g in total of the continuously melt-dried DOG having a water content of 2% by mass (purity: 97% mass) was obtained.

Subsequently, 1,800 g of the foregoing continuously melt-dried DOG was charged into a stirring tank having an internal volume of 3 L while holding it at a temperature of 140° C. and subjected to vacuum-drying under the following conditions.
[Vacuum-Drying Condition]
Stirring rotation number: 200 rpm
Fluidization means: Semicircular blade rotating around an axis
Temperature: 140° C.
Pressure: 8 kPa
Time: 2 hours In the following relational expression between the temperature X (° C.) and the pressure Y [kPa (abs)]:

$$10^{(-3708.7/(X+230)+9.11)} \leq Y \leq 0.0025\exp^{(0.0574X)}+10$$

the left-side is calculated to be 0.016, and the right-side is calculated to be 28, resulting in (0.016<Y<28). Thus, the foregoing relational expression is satisfied.

According to the foregoing operation, 1,765 g of dried DOG having a water content of 0.3% by mass (DOG purity: 99% mass) was obtained.
[Flake Molding]

Furthermore, the dried DOG in a molten state as obtained in the foregoing method was cooled with water at 20° C. and introduced into a drum flaker having a peripheral speed of the drum of 4 m/min in a dip feed manner, thereby producing 100 kg/h·m² of flake-shaped DOG having an area of the surface portion of from 0.5 to 3 cm² and a thickness of from 0.5 to 1 mm.

Example 2

The liquid-containing raw material DOG was continuously melt-dried under the same condition as in Example 1 and subsequently subjected to ventilation-drying under the following condition.
[Ventilation-Drying Condition]
Stirring rotation number: 200 rpm
Fluidization means: Semicircular blade rotating around an axis
Temperature: 140° C.
Pressure: Normal pressure
Ventilation gas: Nitrogen (20° C.)
Ventilation rate of gas: 0.03 m³/h (in a standard state)
Time: 2 hours
Total ventilation amount of gas: 0.03 (m³/h)×2 (h)=0.06 m³
Volume of continuously melt-dried DOG to be fed: 0.5 (kg)/105 (kg/L) (specific gravity)=0.00048 m³
Volume ratio {(total ventilation amount of gas)/(volume of liquid-containing DOG to be fed): 125 times According to the foregoing operation, dried DOG having a water content of 0.3% by mass (DOG purity: 99% mass) could be obtained.
[Flake Molding]

Furthermore, the dried DOG in a molten state as obtained in the foregoing method was cooled with water having a temperature of 40° C. and introduced into a drum flaker having a peripheral speed of the drum of 4 m/min in a dip feed manner, thereby producing 80 kg/h·m² of flake-shaped DOG having an area of the surface portion of from 0.5 to 3 cm² and a thickness of from 0.6 to 1.2 mm.

Example 3

An experiment was carried out in the same manner as in Example 1, except that the temperature and the pressure in the vacuum-drying step were 155° C. and 15 kPa, respectively. As a result, 1,764 g of dried DOG having a water content of 0.3% by mass (DOG purity: 99% mass) could be obtained; and 65 kg/h·m² of flake-shaped DOG having an area of the surface portion of from 0.5 to 3 cm² and a thickness of from 0.7 to 1.5 mm could be produced.

Example 4

An experiment was carried out in the same manner as in Example 1, except that the temperature and the pressure in the vacuum-drying step were 150° C. and 10 kPa, respectively. As a result, 1,750 g of dried DOG having a water content of 0.2% by mass (DOG purity: 99% mass) could be obtained; and 100 kg/h·m² of flake-shaped DOG having an area of the surface portion of from 0.5 to 3 cm² and a thickness of from 0.5 to 1 mm could be produced.

Example 5

An experiment was carried out in the same manner as in Example 1, except that the temperature and the pressure in the vacuum-drying step were 145° C. and 10 kPa, respectively. As a result, 1,760 g of dried DOG having a water content of 0.3% by mass (DOG purity: 99% mass) could be obtained; and 110 kg/h·m² of flake-shaped DOG having an area of the surface portion of from 0.5 to 3 cm² and a thickness of from 0.4 to 0.7 mm could be produced.

Example 6

An experiment was carried out in the same manner as in Example 1, except that the temperature and the pressure in the vacuum-drying step were 135° C. and 3 kPa, respectively. As a result, 1,745 g of dried DOG having a water content of 0.2% by mass (DOG purity: 99% mass) could be obtained; and 120 kg/h·m² of flake-shaped DOG having an area of the surface portion of from 0.5 to 3 cm² and a thickness of from 0.3 to 0.6 mm could be produced.

Example 7

An experiment was carried out in the same manner as in Example 1, except that the temperature and the pressure in the vacuum-drying step were 130° C. and 3 kPa, respectively. As a result, 1,755 g of dried DOG having a water content of 0.3% by mass (DOG purity: 99% mass) could be obtained; and 100 kg/h·m² of flake-shaped DOG having an area of the surface portion of from 0.5 to 3 cm² and a thickness of from 0.5 to 1 mm could be produced.

Comparative Example 1

An experiment was carried out in the same manner as in Example 1, except that the temperature and the time in the continuous melt-drying step were changed to 180° C. and 3 hours, respectively and that the vacuum-drying was not carried out. As a result, though the purity of DOG was 98.5% by mass, the water content of DOG was 0.8% by mass. Thus, the resulting DOG was an off-spec as a product.

Also, though flake-shaped DOG could be produced, the water content was high so that the resulting DOG was of no utility value.

Comparative Example 2

An experiment was carried out in the same manner as in Example 1, except that 2000 g of the liquid-containing raw material DOG (water content: 23% by mass) as obtained in Referential Example 1 was charged in a stirring tank having an internal volume of 3 L; that the temperature in the continuous melt-drying step was changed to 200° C.; and that the vacuum-drying was not carried out. As a result, though dried DOG having a water content of 0.3% by mass could be produced, the purity of DOG was 94% by mass. Thus, the resulting DOG was an off-spec as a product.

Also, though flake-shaped DOG could be produced, the purity was low so that the resulting DOG was of no utility value.

Comparative Example 3

An experiment was carried out in the same manner as in Example 1, except that the continuous melting step was omitted. As a result, though the purity of DOG was 99% by mass, it was difficult to efficiently remove a large amount of water. Therefore, it took 15 hours until the water content reached 2% as that after the continuous melting step in Example 1.

Comparative Example 4

An experiment was carried out in the same manner as in Example 2, except that the continuous melting step was omitted. As a result, though the purity of DOG was 99% by mass, and though the total ventilation amount of the gas was 0.1 m³, the water content was 1.0% by mass. Thus, the resulting DOG was an off-spec as a product.

Also, though flake-shaped DOG could be produced, the water content was high so that the resulting DOG was of no utility value.

Comparative Example 5

An experiment was carried out in the same manner as in Example 1, except that the pressure of the vacuum-drying was 35 kPa. As a result, though the purity of DOG was 98.5% by mass, the water content of DOG was 0.8% by mass. Thus, the resulting DOG was an off-spec as a product. Also, though flake-shaped DOG could be produced, the water content was high so that the resulting DOG was of no utility value.

Comparative Example 6

An experiment was carried out in the same manner as in Example 1, except that the temperature and the pressure in the vacuum-drying step were 130° C. and 28 kPa, respectively. As a result, though the purity of DOG was 98.9% by mass, the water content of DOG was 0.5% by mass. Thus, the resulting DOG was an off-spec as a product. Also, though flake-shaped DOG could be produced, the water content was high so that the resulting DOG was of no utility value.

Comparative Example 7

An experiment was carried out in the same manner as in Example 2, except that the ventilation rate of gas in the ventilation-drying step was 0.002 m³/h. As a result, though the purity of DOG was 98.5% by mass, the water content was 0.8% by mass. Thus, the resulting DOG was an off-spec as a product. Also, though flake-shaped DOG could be produced, the water content was high so that the resulting DOG was of no utility value.

In the light of the above, different from usual compounds, according to the liquid-containing raw material DOG, by combining the continuous melting step with the vacuum-drying step or ventilation-drying step under the specified condition as in Examples 1 to 7, the liquid content could be reduced to not more than 0.5% by mass, and moreover, not more than 0.3% by mass, and in addition thereto, dried DOG with a high purity could be obtained. On the other hand, it is understood that the drying condition which is considered to be sufficient at a glance in usual compounds as in Comparative Examples 1 to 7 is inadequate as a drying method of the liquid-containing raw material DOG.

Referential Example 2

The liquid-containing raw material DOG as obtained in Referential Example 1 was subjected to the vacuum-drying step at 25° C., thereby obtaining 600 kg of powered DOG (water content: 0.2% by mass). This DOG was heated in a reactor equipped with a jacket and a stirrer and having an internal volume of 6 m³. As a result, when the temperature of the jacket was 160° C., the whole could not be melted. Thus, the temperature was raised to 170° C., thereby melting the DOG. As a result, the purity of the melted liquid-containing raw material DOG decreased to 94% by mass.

INDUSTRIAL APPLICABILITY

The dried DOG obtained in the present invention is a polyhydric alcohol having a special structure having two primary hydroxyl groups, a neo structure and a cyclic acetal and can be used as an intermediate or a monomer of polymer materials such as poly(meth)acrylates, polycarbonates, polyesters, polyurethanes, polyether polyols, epoxy resins, etc. and furthermore, as a raw material of photocurable resins, adhesives, photocurable inks, plasticizers, resin stabilizers, lubricating oils, paints, etc.

The invention claimed is:
1. A method for producing flake-like dried 2-(5-ethyl-5-hydroxymethyl-1,3-dioxan-2-yl)-2-methylpropan-1-ol (hereinafter referred to as "DOG") represented by the following formula:

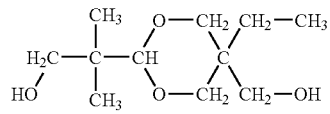

which comprises making DOG containing from 10 to 50% by mass of a liquid (hereinafter abbreviated as "liquid-containing raw material DOG") go through the following continuous melt-drying step (i), to obtain DOG having a liquid content of from 0.8 to 5% by mass (hereinafter abbreviated as "continuously melt-dried DOG"); making the continuously melt-dried DOG go through the following vacuum-drying step (ii) or the following ventilation-drying step (iii) while holding a molten state thereof, to obtain DOG whose liquid content is reduced to not more than 0.5% by mass (hereinafter referred to simply as "dried DOG"); and flaking the obtained dried DOG in a flake production step:

(i) Continuous melt-drying step: a continuous melt-drying step of heat melting the liquid-containing raw material DOG in the range of a temperature which is the higher of a melting point of the liquid-containing raw material DOG and a boiling point of the liquid, or higher and not higher than 160° C. (hereinafter referred to as "melt temperature range"), to remove the liquid and feeding the residue into a next step and at the same time, continuously or intermittently feeding the non-molten liquid-containing raw material DOG into a molten liquid-containing raw material DOG such that the temperature of the whole liquid-containing raw material DOG does not fall outside the melt temperature range, thereby regulating the liquid content of DOG to be continuously or intermittently fed into a next step to 0.8 to 5% by mass;

(ii) Vacuum-drying step: a vacuum-drying step in which a relation between a temperature X (° C.) and a pressure Y [kPa (abs)] is satisfied with the following expression:

$$10^{(-3708.7/(X+230)+9.11)} \leq Y \leq 0.0025\exp^{(0.0574X)}+10,$$

wherein X is from 125 to 160; and (iii) Ventilation-drying step: a ventilation-drying step of not only ventilating a gas at from 10 to 160° C. for 0.5 hours or more but regulating the total ventilation amount of the gas relative to the continuously melt-dried DOG charged in the ventilation drying step to 10 times or more (volume ratio) and carrying out the foregoing in the melt temperature range.

2. The method for producing flake-like dried DOG according to claim 1, wherein the liquid is water.

* * * * *